(12) United States Patent
Vaidyanathan et al.

(10) Patent No.: US 6,658,914 B2
(45) Date of Patent: Dec. 9, 2003

(54) METHOD AND APPARATUS FOR CHARACTERIZING ROLL STRUCTURE

(75) Inventors: Nandakumar Vaidyanathan, Litchfield, NH (US); Robert Bruce Lowd, Chestnut Hill, MA (US); Brian Roland Lamoureux, Pelham, NH (US); Stephen Dana Federico, Wayland, MA (US)

(73) Assignee: Presstek, Inc., Hudson, NH (US)

( * ) Notice: Subject to any disclaimer, the term of this patent is extended or adjusted under 35 U.S.C. 154(b) by 5 days.

(21) Appl. No.: 10/090,545

(22) Filed: Mar. 4, 2002

(65) Prior Publication Data

US 2003/0164022 A1 Sep. 4, 2003

(51) Int. Cl.[7] .................................................. G01M 7/00
(52) U.S. Cl. .................................................... 73/12.05
(58) Field of Search ............................. 73/12.01, 12.04, 73/12.05, 12.06, 12.07, 12.08, 12.09, 12.11

(56) References Cited

U.S. PATENT DOCUMENTS

| | | | | |
|---|---|---|---|---|
| 4,147,055 A | * | 4/1979 | Wood et al. | 73/167 |
| 4,218,922 A | | 8/1980 | Ensminger | 73/588 |
| 4,500,051 A | * | 2/1985 | Cottle, Jr. et al. | 244/3.16 |
| 4,594,880 A | | 6/1986 | Murdoch et al. | 73/32 |
| 4,676,094 A | | 6/1987 | Hoffmann et al. | 73/78 |
| 4,845,989 A | | 7/1989 | Titlow et al. | 73/597 |
| 5,218,161 A | * | 6/1993 | Martin | 89/8 |
| 5,339,737 A | | 8/1994 | Lewis et al. | 101/454 |
| 5,535,627 A | | 7/1996 | Swanson et al. | 73/597 |
| 5,755,905 A | | 5/1998 | Sinn et al. | 156/184 |
| 6,048,280 A | * | 4/2000 | Palmer et al. | 473/416 |

OTHER PUBLICATIONS

Swanson, R.P., *Determination of Wound Roll Structure Using Acoustic Time of Flight Measurement*, Proceedings of the First International Conference on Web Handling, (May 19–22, 1991), pp. 57–67.

Swanson, R.P., *Determination of Wound Roll Structure Using Acoustic Time of Flight Measurement*, M. S. Thesis, Web Handling Research Center, College of Engineering, Architecture and Technology, Oklahoma State University, (May 1992), pp. 1–136.

Kaiser, M.A., *Advancements in the Split Hopkinson Bar Test*, M. S. Thesis Virginia Polytechnic Institute and State University, (May 1, 1998), pp. 1–85.

Walley, S.W., *DYMAT 2000 Series—Waves in Rods*, [retrieved in 2001], Retrieved from the Internet: <URL: http://www.etca.fr/dymat/utml/body_waves.html>.

Kuokkala, V. et al., *Electron Microscopy, Hopkinson Split Bar (HSB)* 2001 [retrieved in 2001], Retrieved from the Internet: <URL: http://www.tut.fi/units/ms/elm/laittect/hopkinson(eng).htm>.

* cited by examiner

Primary Examiner—Max Noori
(74) Attorney, Agent, or Firm—Testa, Hurwitz & Thibeault, LLP

(57) ABSTRACT

A system for imparting and detecting mechanical energy includes a projectile and a hollow tube allowing the projectile to move therein. A portion of the projectile is allowed to emerge from one end of the tube and thereby transfer mechanical energy to a receiving entity, e.g., a wound roll of material. An actuator drives the projectile through the tube, and a first sensor detects when the protruding portion of the projectile extends from the tube to make contact with, for example, the core of the wound roll to start a timing sequence. A second sensor detects the arrival of the mechanical energy at, for example, the roll surface so that a comparison can be made between the start and end times.

16 Claims, 6 Drawing Sheets

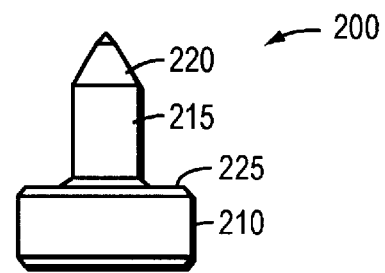
FIG. 2
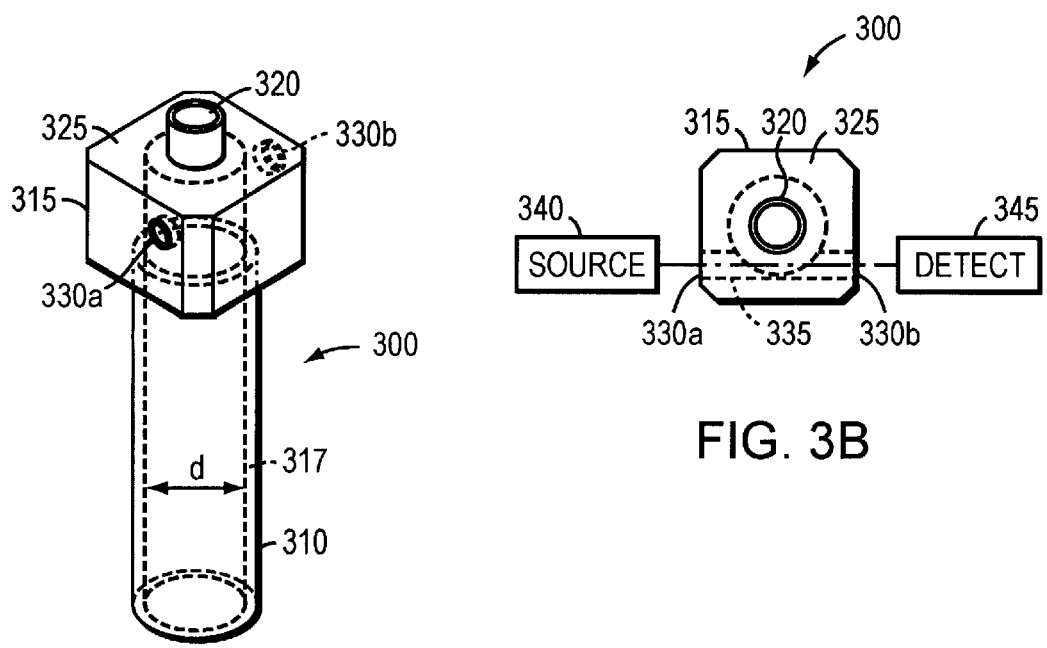
FIG. 3A
FIG. 3B

METHOD AND APPARATUS FOR CHARACTERIZING ROLL STRUCTURE

BACKGROUND OF THE INVENTION

1. Field of the Invention

This invention relates generally to handling wound rolls of material and, in particular, for determining the internal structure of a wound roll.

2. Background of the Invention

In industries, such as the printing industry, that utilize wound rolls ("webs") of material, it is advantageous to be able to determine the internal structure of such rolls. Before time and resources are directed to converting a wound roll of material into a finished product, a determination of the wound roll's internal structure allows a processor to know whether the wound roll is of sufficient quality to warrant conversion. Structural characterization of a roll also helps ensure that problematic wound rolls that could damage sensitive machinery are not processed.

One standard approach in the prior art to determining the internal structure of a wound roll is to use a device based on a split hopkinson pressure bar in order to measure the time of flight of mechanical energy through the roll. A split hopkinson pressure bar consists of two projectiles located within a hollow tube. The first projectile is a simple cylindrical plug of material that is free to travel within the tube. The second projectile is located at one end of the tube and can move only within a narrow range inside the tube. In operation, one end of the second projectile is in contact with the wound roll of material. To determine the internal structure of the wound roll, the first projectile is sent down the tube and impacts the second projectile. The second projectile thereupon impacts the wound roll, imparting mechanical energy thereto. A sensor records the impact of the second projectile on the wound roll.

This approach suffers from several disadvantages. First, the first projectile is susceptible to becoming jammed in the tube. This is due to the deformation of the first projectile that occurs when it impacts the second projectile. Second, the second projectile is also susceptible to becoming jammed due to the deformation of structures used to guide and retain it. As a result, each time either projectile becomes jammed, the system must be disassembled and the deformed projectile replaced.

Accordingly, there is a need for a system for imparting mechanical energy to a wound roll that is reliable, convenient to operate, and easily maintained.

DESCRIPTION OF THE INVENTION

SUMMARY OF THE INVENTION

An apparatus in accordance with the present invention includes a specially designed single projectile for imparting mechanical energy to a wound roll. The use of a single projectile significantly reduces its operational deformation. Moreover, the shape of the projectile ensures that all or nearly all of the projectile's mechanical energy is transferred to the wound roll. This means that little mechanical energy remains for deformation. The projectile's shape helps to guide it smoothly within the tube, thereby further reducing the possibility that it can become jammed, and also improves the signal-to-noise ratio. A sensor arrangement provides clear signals, and the projectile's unibody nature simplifies replacement.

According to one aspect, the invention comprises a system for imparting and detecting mechanical energy. An embodiment of the system includes a projectile and a hollow tube allowing the projectile to move therein. A portion of the projectile is allowed to emerge from one end of the tube and thereby transfer mechanical energy to a receiving entity, e.g., a wound roll of material. An actuator drives the projectile through the tube, and a first sensor detects when the protruding portion of the projectile extends from the tube to make contact with, for example, the core of the wound roll to start a timing sequence. A second sensor detects the arrival of the mechanical energy at, for example, the roll surface so that a comparison can be made between the start and end times.

According to another aspect, the invention relates to a method of imparting and detecting mechanical energy. In one embodiment, the method comprises sending a projectile down a hollow tube from a first end to a second end thereof. The second end of the tube allows a portion of the projectile to protrude beyond the tube to transfer mechanical energy to a receiving entity. Mechanical energy from the projectile is transferred to the receiving entity, and this transfer is sensed. In addition, the method comprises sensing the transferred mechanical energy in the receiving entity. The method facilitates, and may include, calculating time-of-flight information for the mechanical energy traveling through the receiving entity.

BRIEF DESCRIPTION OF THE DRAWINGS

The above and further advantages of the invention may be better understood by referring to the following description taken in conjunction with the accompanying drawings, in which:

FIG. 2 is an enlarged side elevation of a projectile in accordance with the invention;

FIG. 3A is a perspective view of a barrel for receiving and facilitating travel of the projectile shown in FIG. 2;

FIG. 3B is a plan view of the barrel illustrated in FIG. 3A, with an optical detection path or channel shown in phantom;

It should be emphasized that the drawings or elements thereof are not necessary drawn to scale.

DETAILED DESCRIPTION OF THE PREFERRED EMBODIMENTS

Figure 1:
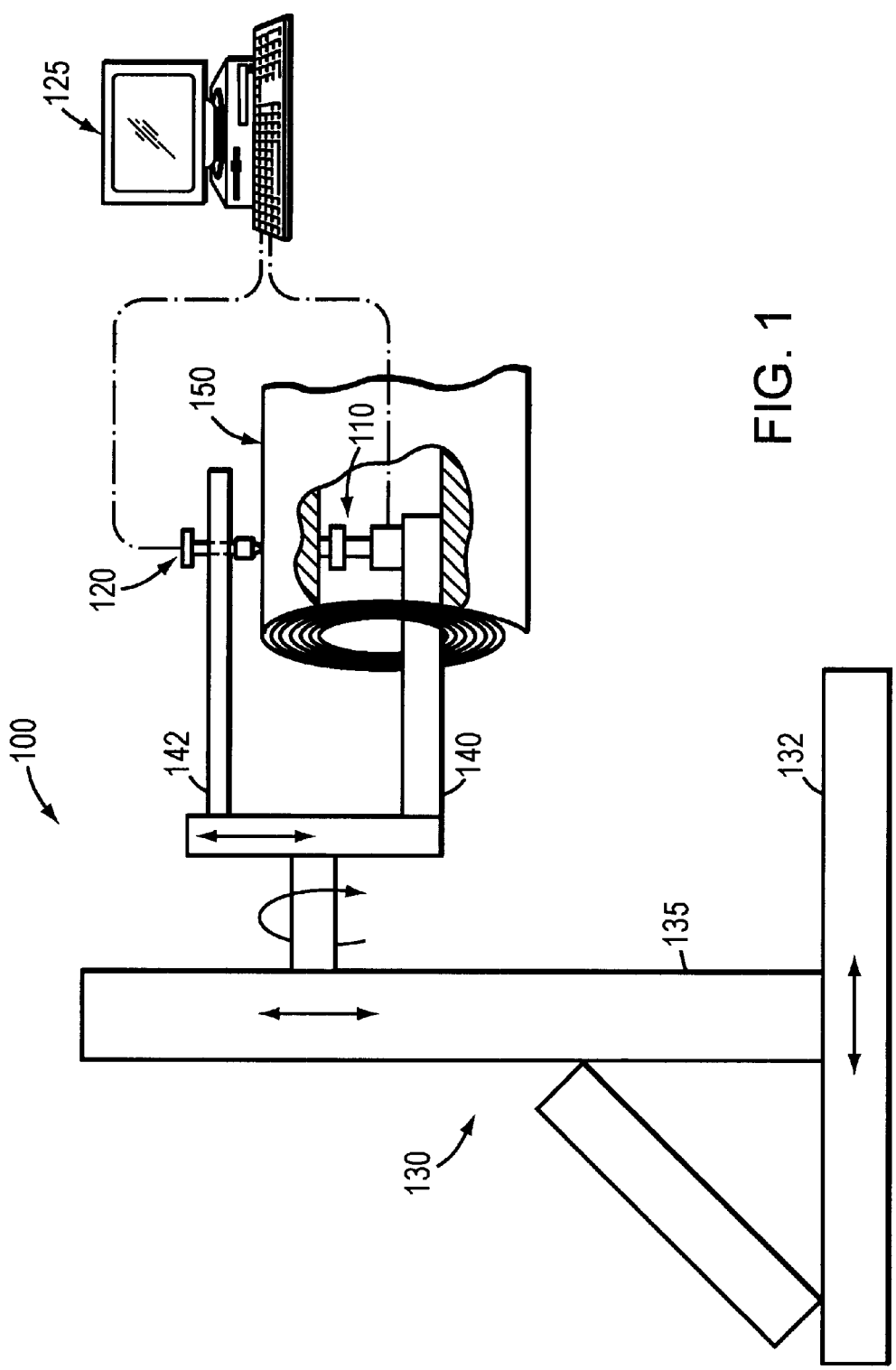
FIG. 1 is a partial-cutaway side elevation of a system in accordance with the invention.

Refer first to FIG. 1, which illustrates a system in accordance with the invention and a representative environment for its operation. The depicted embodiment includes an energy-transfer unit 110 and an energy detector 120. These components are in communication with a suitably programmed computer 125, which receives information therefrom and analyzes it as described in greater detail below. A configurable support fixture 130 includes a base 132, a tower 135 projecting vertically from the base and, as indicated in the figure, preferably capable of horizontal movement with respect thereto. Support fixture 130 also includes a pair of elongated platforms 140, 142. As indicated, platform 142 is vertically movable relative to platform 140, and both platforms 140, 142 may be rotatable relative to tower 135 and vertically movable therealong.

In a preferred embodiment of the invention, energy-transfer unit 110 rests on platform 140 and is received within the core of a roll 150 of material to be analyzed (as shown by the cut-away portion of roll 150). Thus, platform 140 is narrow enough to fit within cores having varying diameters. Detector 120 is borne by platform 142, and extends therethrough so as to contact the exterior surface of roll 150. In this way, energy imparted to the core of roll 150 may be detected when it reaches the exterior of roll 150. It should be understood, however, that although transmission of energy to the roll 150 through the core is preferred in order to avoid damage to the wound material, it is equally possible to exchange the locations of energy-transfer unit 110 and detector 120, so that the latter resides within the core and energy is imparted to the exterior surface of roll 150.

Refer now to FIG. 2, which illustrates a projectile 200 in accordance with the invention. The projectile 200, which is generally fabricated (e.g., machined or cast) from metal or other sturdy, impact-resistant material, includes a base portion 210 and a shank portion 215. Shank portion 215 terminates in a tip 220 having a contour whose dimensions are dictated by the desire to minimize any mismatch in acoustic impedance between the tip 220 and the impact surface, and in particular to produce a narrow acoustic beam with minimal dispersion as well as to minimize the impulse time of the impact. A narrow tip 220 helps focus the transmitted energy, but if the tip is too sharp, it may penetrate the impact surface (increasing the impact time). As a practical matter, it is found that greater tip bluntness becomes more tolerable as the curvature of the impact surface increases. Stated oppositely, at some point dictated by the impact-surface curvature, increased tip sharpness fails to significantly improve the observed signal. Those of skill in the art can readily determine without undue experimentation the optimal dimensions of tip 220 for a particular application.

With reference to FIGS. 2, 3A and 3B, projectile 200 travels within a barrel 300. The illustrated barrel 300 includes a cylinder portion 310 and, over one end thereof, a detection structure 315. The interior diameter d of barrel 300 remains constant through both the cylinder portion 310 and the detection structure 315, forming a long tube segment 317. Diameter d is slightly larger than the diameter of the base portion 210 of projectile 200, allowing it to travel within tube segment 317 on air lubrication. A narrower exit tube segment 320 extends from the otherwise solid top wall 325 of detection structure 315. The interior diameter of exit segment 320 is slightly larger than the diameter of the shank portion 215 of projectile 200, allowing the shank to travel within the exit segment on air lubrication, but is substantially narrower than projectile base 210. Consequently, top wall 325 forms a shoulder that limits the extent of vertical movement of projectile 200 within barrel 300. The height of exit segment 320 is chosen such that projectile tip 220 can protrude beyond the rim of exit segment 320 with the top surface 225 of projectile base 210 retained against the interior surface of top detection-structure wall 325.

A pair of detection apertures 330a, 330b facilitate optical communication with tube segment 317 via a bore 335, which defines an optical channel (shown in phantom in FIG. 3B) extending from tube segment 317 to each of the detection apertures. As illustrated in FIG. 3B, the diameter of bore 335 is such that the optical channel does not extend into the region defined by exit segment 320. A source 340 may send an optical signal (e.g., an infrared beam) through the optical channel for detection by a detector 345.

Figure 4A:
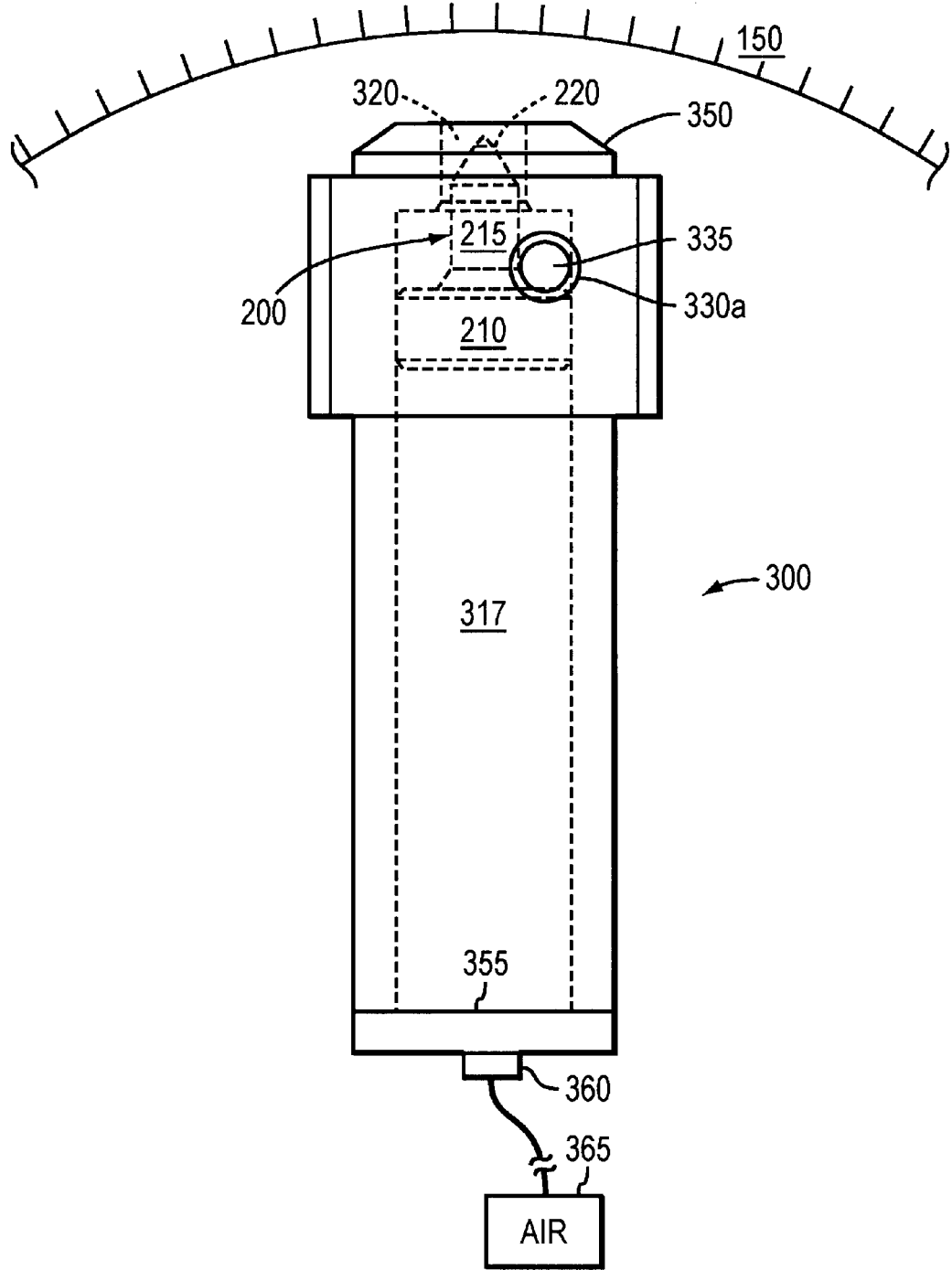
FIG. 4A is an elevation of a projectile traveling within the barrel shown in FIGS. 3A, 3B just prior to optical detection.
Figure 4B:
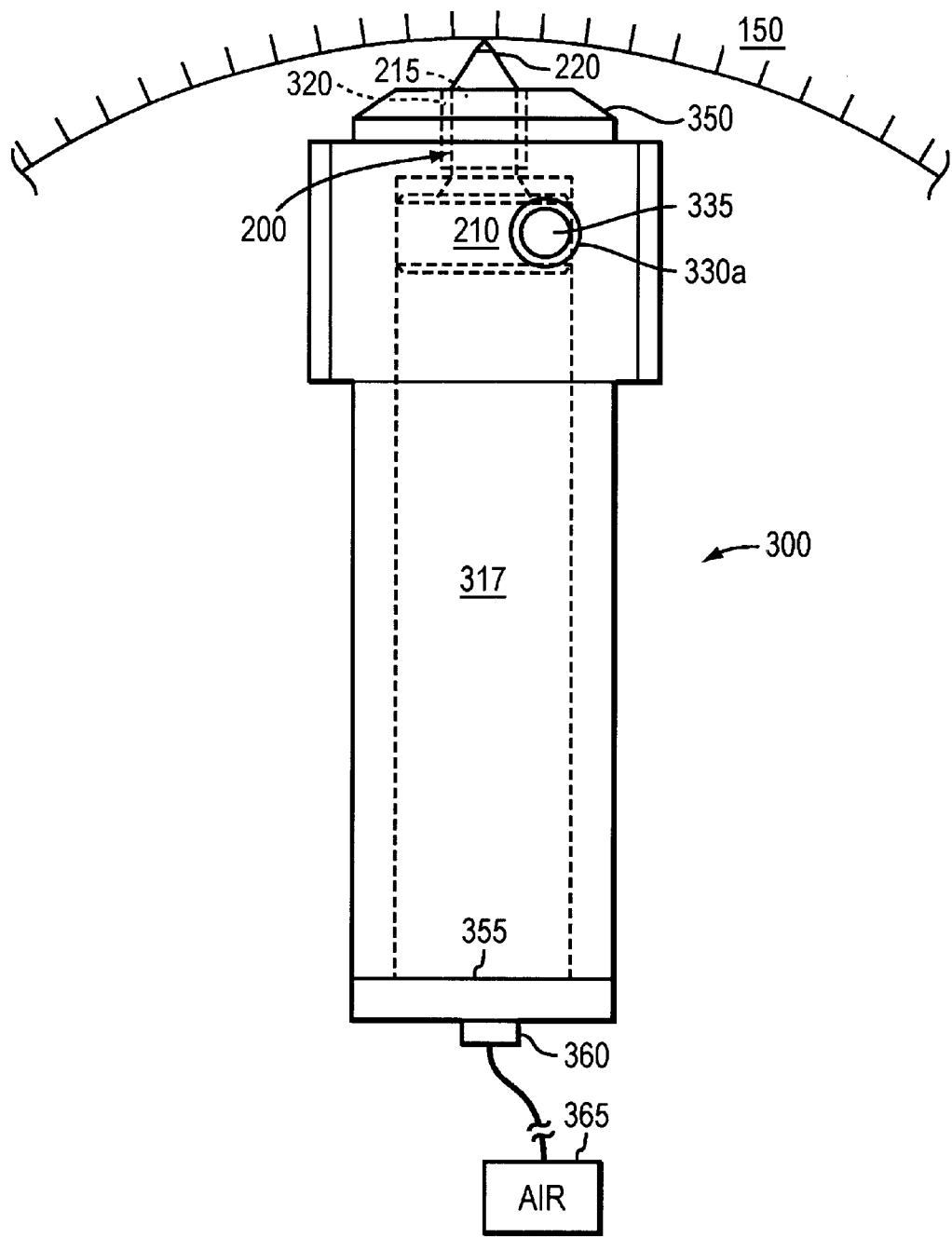
FIG. 4B is an elevation of a projectile traveling within the barrel shown in FIGS. 3A, 3B and fully blocking the optical detection path.

FIG. 4A illustrates the manner in which projectile 200 travels within barrel 300. For operational convenience and structural integrity, exit segment 320 is defined not as an exterior tube 320, but as a broad integral capping piece 350. As shown, the bottom end of barrel 300 is sealed with a plug 355, which has an inlet port 360 in fluid communication with a compressed air source 365. Projectile 200 ordinarily rests on the interior surface of plug 355. A timed burst of compressed air at a predetermined pressure sends projectile 200 upward. When it reaches the illustrated position, projectile base 210 just begins to enter the optical channel defined by bore 335. Due to the positioning and diameter of bore 335, projectile shank 215 does not enter the optical channel and its passage is therefore not detected by detector 345 (FIG. 3B). In FIG. 4B, projectile base 210 fully occludes the optical channel as projectile tip 220 strikes the interior surface of the core of roll 150. As illustrated, the distance between the top of bushing 350 and the interior core surface is such that projectile 200 has not traveled fully through tube segment 317 (that is, the top surface 225 of projectile base 210 has not reached the shoulder formed at the top of tube segment 317) when it strikes the interior core surface. This prevents damage to top surface 225 and consequent deformation of the projectile.

Figure 5:
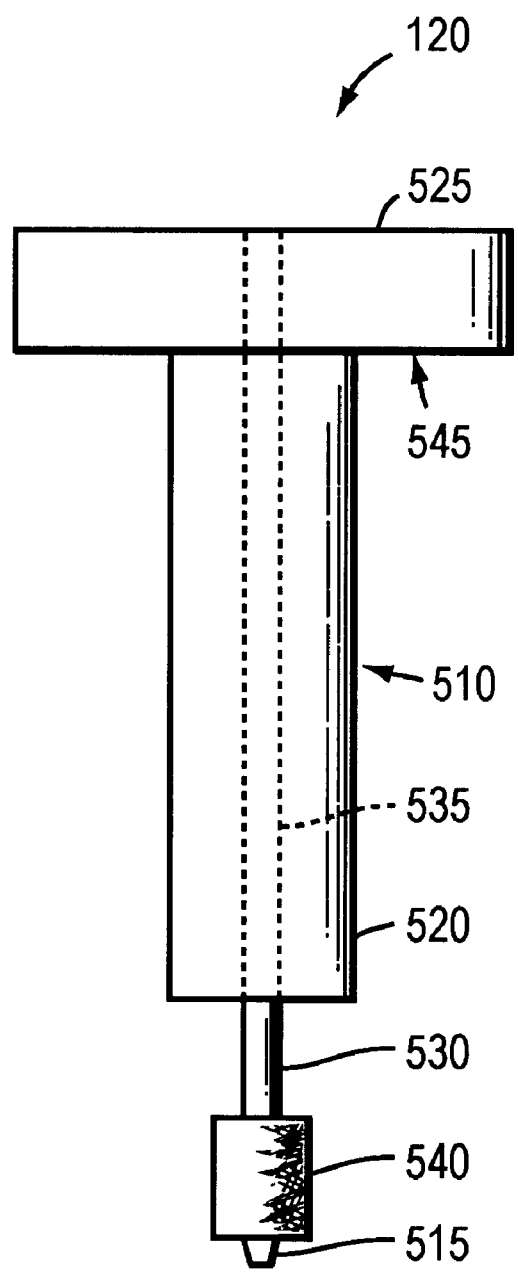
FIG. 5 is an elevation of a detector in accordance with the present invention.

FIG. 5 illustrates a form of detector 120 suitable for use in the present invention. An acoustic detector may utilize an accelerometer in contact with the transmission medium (in this case, roll 150). It is found, however, that rigid mechanical association of the accelerometer with the support structure 100 can interfere with its operation, since the resulting stiffness will itself diminish the detected mechanical energy. At the same time, the accelerometer should remain in stable contact with the transmission medium to receive the energy and produce a clean detection signal.

With reference to FIGS. 1 and 5, the detector 120 includes a retaining body 510 and a detection tip (preferably an accelerometer) 515. Body 510 includes an elongated portion 520 and a bearing portion 525. Elongated portion 520 terminates in a narrower throat 530, the diameter of which preferably matches or approaches that of detection tip 515. A bore 535 extends through the entirety of retaining body 510, facilitating electrical connection through the body to detection tip 515 by means of suitable cables.

Tip 515 is connected to throat 530 by means of a compliant, flexible sleeve 540, which provides mechanical isolation. That is, sleeve 540 prevents tip 515 from being associated with body 520 with excessive stiffness. In addition, body 515 is only loosely associated with support fixture 130, further isolating tip 515 from that structure. Elongated portion 520 slips through a bore extending through platform 142, and the bottom surface 545 of bearing portion 525 preferably rests slightly above the top surface of platform 142 to provide a constant static force with tip 515 against the outer surface of roll 150. This configuration is readily obtained in practice because platform 142 is movable relative to the rest of fixture 130. With detector 120 unsecured to support fixture 130 and tip 515 isolated from retaining body 510 by flexible sleeve 540, detector tip 515 may efficiently receive energy transmitted through roll 150.

Figure 6:
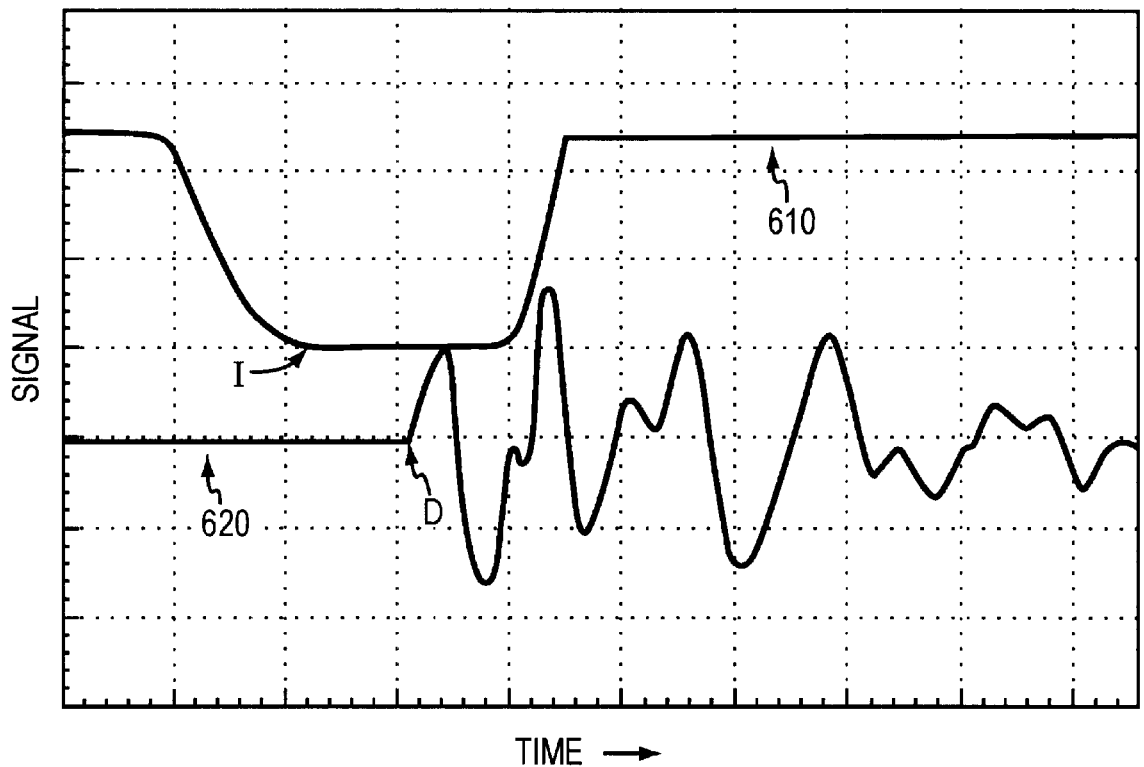
FIG. 6 is a signal trace showing the detection signals used in the operation of the invention.

Operation of the illustrated embodiment of the invention may be understood with reference to FIG. 6, which illustrates representative detection signals, and FIGS. 1 and 4B. The roll 150 is transported by means of a forklift or dolly into proximity with the fixture 130, and the height of platforms 140, 142 is adjusted so that energy-transfer unit 110 may be received within the core of roll 150 as it approaches fixture 140; detector 120 is safely above the outer surface of core 150 or is withdrawn from platform 142 during this operation. With reference to FIG. 4B, air source 365 is actuated to raise projectile 200 until tip 220 just fully protrudes beyond bushing 350 (i.e., so that the entire tapered tip, but none of the shank, of projectile 200 has emerged). As shown in the figure, this position exactly corresponds to full blockage of the optical channel by projectile base 210. The height of platform 140 is then adjusted to bring tip 220 into contact with the interior surface of the core of roll 150. The energy-transfer unit 110 is then properly positioned for use.

With detector 120 placed through platform 142, the height of this platform is adjusted so that the tip 515 of detector 120 just touches the outer surface of roll 150, with bottom surface 545 of bearing portion 525 resting on the top surface of platform 142.

Using standard control software, computer 135 actuates air source 365 (FIG. 3), sending projectile 200 upward, and also monitors signals from optical detector 345 (FIG. 3B) and acoustic detector 120. As shown in FIG. 6, the signal 610 from optical detector 345 falls as base portion 210 of projectile 200 occludes progressively more of the optical channel in detection structure 315, until signal 610 reaches a minimum that represents total occlusion and indicates that the projectile has struck the inner core of roll 150. (The signal recovers as projectile 200 falls back through tube segment 317.) The imparted energy travels as an acoustic wave through roll 150 until it is detected a short time later as a disturbance in signal 620 from detector 120. Computer 125 measures the time of flight by subtracting the time of impact I from the time D at which signal 620 first rises.

Although a vertical orientation is preferred for barrel 300 when measurements are made, the rotatability of platforms 140, 142 allows multiple measurement operations to be performed on the same roll 150 at different circumferential positions. This is useful, for example, to test the homogeneity of the roll 150. A non-horizontal orientation is preferred for all measurements so that projectile 200 readily falls back to the bottom plug 355 of barrel 300.

It will therefore be seen that the foregoing apparatus and techniques provide a basis for improved characterization of roll structure. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A system for imparting and detecting mechanical energy, the system comprising:
   (a) a projectile;
   (b) a hollow tube having a first end and a second end and allowing the projectile to move therein from the first end to the second end, the second end allowing a portion of the projectile to protrude therefrom to transfer mechanical energy to a receiving entity;
   (c) an actuator for driving the projectile through the tube;
   (d) a first sensor detecting the impact; and
   (e) a second sensor detecting the mechanical energy transferred to the receiving entity.

2. The system of claim 1 wherein the receiving entity is a wound roll of material, the second sensor detecting, at a surface of the wound roll of material, mechanical energy transferred through the material.

3. The system of claim 1 further comprising an analyzer computing time-of-flight information for mechanical energy imparted to a wound roll by the projectile and traveling therein, based on information from the first and the second sensors.

4. The system of claim 1 wherein the projectile has a shank portion and a base portion, the shank portion tapering to a tip having a curvature.

5. The system of claim 1 wherein the projectile travels in the hollow tube on air lubrication.

6. The system of claim 1 wherein the actuator comprises a source of compressed air and a conduit for controllably delivering the air into the hollow tube.

7. The system of claim 1 wherein the first sensor senses when the portion of the projectile protrudes from the second end of the hollow tube to an extent indicating occurrence of the impact.

8. The system of claim 1 wherein the first sensor is an optical sensor.

9. The system of claim 1 wherein the second sensor comprises a detector flexibly attached to a retaining body, the retaining body being configured to facilitate non-rigid contact between the detector and the receiving entity.

10. A method of imparting and detecting mechanical energy, the method comprising:
    (a) sending a projectile down a hollow tube from a first end to a second end thereof, the second end allowing a portion of the projectile to protrude beyond the tube to transfer mechanical energy to a receiving entity;
    (b) transferring mechanical energy from the projectile to the receiving entity;
    (c) sensing when the projectile transfers mechanical energy; and
    (d) sensing the transferred mechanical energy in the receiving entity.

11. The method of claim 10 wherein the receiving entity is a wound roll of material.

12. The method of claim 11 wherein the mechanical energy is imparted to a core of the material and sensed at a surface of the material.

13. The method of claim 12 further comprising the step computing a time of flight of mechanical energy through the material.

14. The method of claim 10 wherein the projectile travels in the hollow tube on air lubrication.

15. The method of claim 10 wherein the step of sensing when the projectile transfers mechanical energy comprises sensing when a portion of the projectile protrudes from the second end of the hollow tube to an extent indicating contact with the receiving entity.

16. The method of claim 10 wherein the step of sensing when the projectile transfers mechanical energy is accomplished optically.

* * * * *